United States Patent [19]

Ban et al.

[11] 4,435,392
[45] Mar. 6, 1984

[54] 2,5-BENZODIAZOCINE DERIVATIVES AND SALTS THEREOF, AS WELL AS PHARMACEUTICAL AGENT COMPRISING AS EFFECTIVE COMPONENT AT LEAST ONE OF THE DERIVATIVES AND SALTS

[75] Inventors: Masatoshi Ban, Gifu; Kenji Miura, Kasugai; Yutaka Baba, Bisai; Noriyuki Iwata; Akira Fukui, both of Kasugai; Mikio Hori, Gifu; Hajime Fujimura, Kyoto; Eiichi Suenaga, Kunitachi, all of Japan

[73] Assignee: Sanwa Kagaku Kenkyusho Co. Ltd., Aichi, Japan

[21] Appl. No.: 460,649

[22] Filed: Jan. 24, 1983

[30] Foreign Application Priority Data

Mar. 24, 1982 [JP] Japan .................................. 57-45716

[51] Int. Cl.³ ..................... A61K 31/33; C07D 245/06
[52] U.S. Cl. ............................... 424/244; 260/239 BD
[58] Field of Search ................... 260/239 BD; 424/244

[56] References Cited

U.S. PATENT DOCUMENTS

| | | | |
|---|---|---|---|
| 3,499,806 | 3/1970 | Sulkowski | 260/239 BD |
| 3,549,620 | 12/1970 | Houlihan | 260/239 BD |
| 3,565,888 | 2/1971 | Tio | 260/239 BD |
| 3,597,422 | 8/1971 | Winn | 260/239 BD |

FOREIGN PATENT DOCUMENTS

| | | | |
|---|---|---|---|
| 3434M | 7/1965 | France | 260/239 BD |
| 1487344 | 5/1967 | France | 260/239 BD |
| 1093064 | 11/1967 | United Kingdom | 260/239 BD |

*Primary Examiner*—Alton D. Rollins
*Attorney, Agent, or Firm*—Hammond & Littell, Weissenberger and Muserlian

[57] ABSTRACT

A 2,5-benzodiazocine derivative represented by a formula

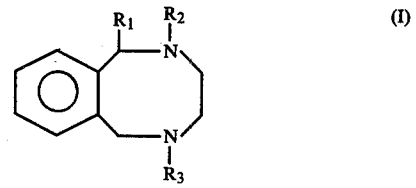

wherein $R_1$ is phenyl or p-methoxyphenyl, $R_2$ is hydrogen or methyl, and $R_3$ is p-methoxyphenethyl, 3-(p-fluorobenzoyl)-propyl, cyclopropylmethyl or

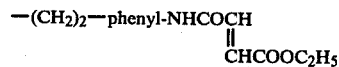

or a salt of such novel compound as well as a CNS-active pharmaceutical agent containing as an effective component at least one of said derivatives and salts.

4 Claims, No Drawings

2,5-BENZODIAZOCINE DERIVATIVES AND SALTS THEREOF, AS WELL AS PHARMACEUTICAL AGENT COMPRISING AS EFFECTIVE COMPONENT AT LEAST ONE OF THE DERIVATIVES AND SALTS

The present invention relates to a novel 2,5-benzodiazocine derivative and a salt thereof, as well as a pharmaceutical agent comprising as effective component at least one of the derivatives and salt.

The derivative is represented by a formula

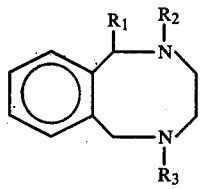

wherein $R_1$ is phenyl or p-methoxyphenyl, $R_2$ is hydrogen or methyl, and $R_3$ is p-methoxyphenethyl, 3-(p-fluorobenzoyl)-propyl, cyclopropylmethyl or

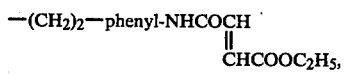

The compounds represented by the formula I and salts thereof show various actions on the nervous system, particularly analgetic, cough curing, antipyretic and sleep depth increasing actions and thus are useful as analgetics, cough cures, antipyretics and sedatives.

The compounds shown by the formula I are novel ones which have not been disclosed in any prior art literature and according to the invention, can be prepared by starting with, for instance, a 1-substituted or unsubstituted phenyl-1,2,3,4,5,6-hexahydro-2,5-benzodiazocine represented by the formula

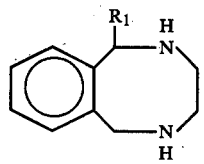

wherein $R_1$ has the meaning as referred to, converting the 5-hydrogen into an organic radical in a manner known per se, such as the acid chloride method, carboxylic acid method, alkylhalogenide method and the like, and if necessary methylating 2-hydrogen in a manner known per se. A suitable protective radical may selectively be used for the methylation in 2-position.

The following compounds can be listed as exemplary ones among the compounds shown by the formula I.

(a) 5-[3-(p-fluorobenzoyl)propyl]-1,2,3,4,5,6-hexahydro-1-(p-methoxyphenyl)-2-methyl-2,5-benzodiazocine

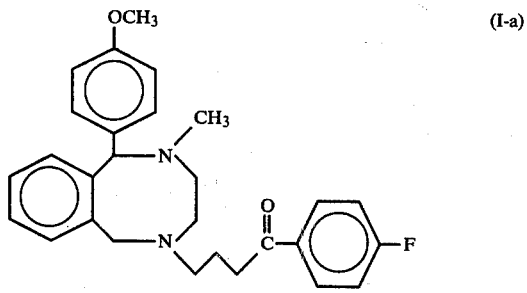

(b) 5-(p-methoxyphenethyl)-1,2,3,4,5,6-hexahydro-1-(p-methoxyphenyl)-2-methyl-2,5-benzodiazocine

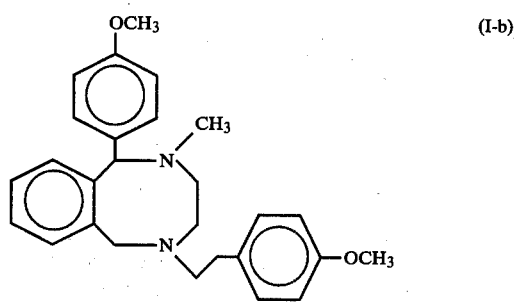

(c) 5-[3-(p-fluorobenzoyl)propyl]-1,2,3,4,5,6-hexahydro-1-phenyl-2-methyl-2,5-benzodiazocine

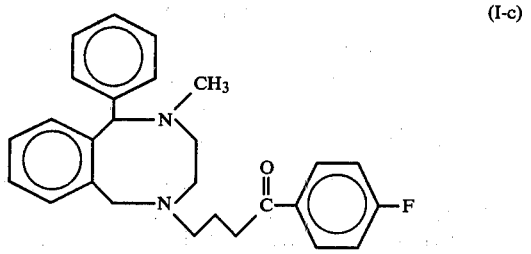

(d) 5-cyclopropylmethyl-1,2,3,4,5,6-hexahydro-1-phenyl-2,5-benzodiazocine

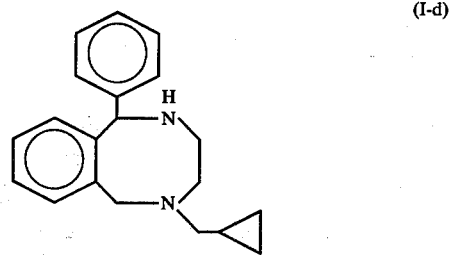

(e) [5(E)]-ethyl-4-[[4-[2-(1,2,3,4,5,6-hexahydro-1-phenyl-2,5-benzodiazocin)-5-yl]ethyl]phenyl]amino-4-oxo-2-butenoate

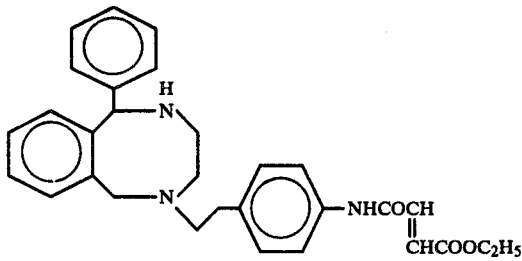

(f) 5-[3-(p-fluorobenzoyl)propyl]-1,2,3,4,5,6-hexahydro-1-(p-methoxyphenyl)-2,5-benzodiazocine

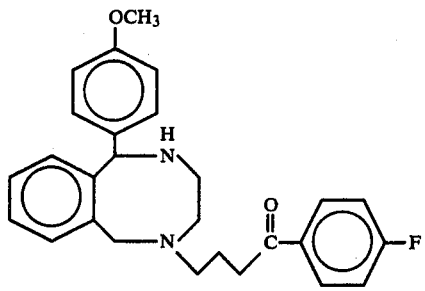

The compounds shown by the formula I and pharmaceutically acceptable salts thereof can be administered by injection, orally or by any conventional route. A dosage for the purpose of medical treatment for an adult varies depending on dosing route and times but is about 5 to 200 mg per day and for instance, in oral dosage, 30 to 40 mg per time is preferable for an adult.

The invention will now be further explained in detail, with reference to Examples.

EXAMPLE 1

5-[3-(p-fluorobenzoyl)propyl]-1,2,3,4,5,6-hexahydro-1-(p-methoxyphenyl)-2-methyl-2,5-benzodiazocine (compound I-a) (hydrochloride)

200 g (745.3 mmol) of 1,2,3,4,5,6-hexahydro-1-(p-methoxyphenyl)-2,5-benzodiazocine, 190 g (776.5 mmol) of 4,4-ethylenedioxy-4-(p-fluorophenyl)-butyl chloride, 80 g (952.3 mmol) of $NaHCO_3$ and 1.5 liter of dimethylformamide were stirred at 100° C. for 4 hours and then the solvent was removed under a reduced pressure. The reaction product was extracted with ethyl ether, washed with water, dried on $Na_2SO_4$. The solvent was distilled off and then the resulting oily substance was refined through a silica gel column chromatography (ethyl ether-ethyl ether/triethylamine=10/1) to obtain 253 g (71.3%) of an intermediate as oily substance.

To a mixture of 53 g (111.2 mmol) of this oily substance, 16.7 g (165.2 mmol) of triethylamine and 60 mg of $CHCl_3$, 100 ml $CHCl_3$ solution of 13.3 g (122.6 mmol) of $ClCOOC_2H_5$ was added in dropwise for 1 hour at room temperature and under inert gas atmosphere and after completion of the addition, the resulting solution was further stirred for 1 hour. The resulting reaction mixture was washed with water, dried on $Na_2SO_4$, and subjected to distillation to remove the solvent. The remaining oily substance was dissolved in 1 liter of ethyl ether, ice-cooled to add 17.5 g of $LiAlH_4$ and then refluxed for 4.5 hours under stirring. The reaction mixture was cooled and 70 ml of 0.8 N-NaOH was added thereto to cause a decomposition of the catalyzer. A forming precipitate was filtered off. The filtrate was washed with $CH_2Cl_2$ and subjected to distillation under a reduced pressure. The remaining oily substance was refined through a silica gel column chromatography ($CH_2Cl_2$-ethyl ether) to obtain 47 g of an oily substance. The oily substance was dissolved in 350 ml of methanol, 375 ml of 2 N-HCl were added thereto and then the resulting solution was stirred at room temperature for 1 hour to obtain 33.2 g of forming crystals. The filtrate was concentrated under a reduced pressure, made into alkali state with ammonia, extracted with $CH_2Cl_2$, dried, subjected to distillation to remove the solvent, and then the remaining oily substance was separated and refined through a silica gel column chromatography (ethyl ether-ethyl ether/triethylamine=10/1) and converted in methanol into its hydrochloride to obtain 8 g thereof in the form of crystal. These crystals were combined (total 41.7 g, yield 52.9%) and then recrystallized from water/ethanol/methylethylketone to obtain the objective compound (chloride) as colorless prism crystals having melting point of 188°-194° C. (dec.). This salt may be made into free base, in a conventional manner.

Elementary Analysis: $C_{28}H_{31}FN_2O_2 \cdot 2HCl \cdot \frac{1}{2}H_2O$; Cal. C 63.35, H 6.48, N 5.30; Found C 63.47, H 6.48, N 5.39.

IR $(\nu_{max}^{KBr})$ cm$^{-1}$:
2550 ($>N^{\oplus}<$), 1680 ($>=O$)

MS:
EI/DI (m/z); 446 (M$^+$), 252 (base)
CI/DI (i-Bu) (m/z); 447 (M+1)
High MS (m/z); $C_{28}H_{31}FN_2O_2$ (M$^+$)
Cal. 446, 2369
Found 446, 2374

NMR (CDCl$_3$) δ ppm:
8.1–7.78 (2H, m, 2,6-positions of benzoyl, Ar—H)
7.4–6.7 (10H, m, Ar—H)
5.2 (1H, s, C1-H)
4.0 (2H, s, C6-H)
3.72 (3H, s, OCH$_3$)
3.18–1.83 (10H, m, Methylene-H excepting C6)
2.28 (3H, s, N—CH$_3$)

EXAMPLE 2

5-[3-(p-methoxyphenethyl)]-1,2,3,4,5,6-hexahydro-1-(p-methoxyphenyl)-2-methyl-benzodiazocine (Compound I-b) (hydrochloride)

To a mixture of 80.0 g (298.5 mmol) of 1,2,3,4,5,6-hexahydro-1-(p-methoxyphenyl)-2,5-benzodiazocine, 42.1 g (416.1 mmol) of triethylamine and 1.2 liter of $CHCl_3$, 250 ml $CHCl_3$ solution of 57.8 g (313.3 mmol) of p-methoxyphenyl-acetyl chloride were added in dropwise for 1.5 hours at internal temperature of $-30°$ C. and under inert gas atmosphere and then the mixture was further stirred at 0° C. for 1 hour. Thereafter the resulting reaction mixture was washed with water, dried on $Na_2SO_4$ and subjected to distillation to remove the solvent.

The remaining oily substance was dissolved in 69 g (1.499 mol) of formic acid. To the solution kept at 60° C. under stirring on water bath, 51 g (0.595 mol) of 35% formaldehyde were added in dropwise for 20 minutes. After completion of the addition, the water bath was removed and then the mixture was further stirred for 30 minutes.

The reaction mixture was poured onto ice blocks, made into an alkali state with use of conc. NH$_4$OH, extracted with CH$_2$Cl$_2$, washed with water, dried on Na$_2$SO$_4$ and then subjected to distillation to remove the solvent. The remaining oily substance was separated and refined through a silica gel column chromatography (CH$_2$Cl$_2$-ethyl ether) to obtain 112 g (87.3%) of an amide.

112 g of the amide were dissolved in 400 ml of anhydrous tetrahydrofuran and the resulting solution was added in dropwise at room temperature for 1.5 hours under inert gas atmosphere into 1.2 liters ethyl ether suspension of 30 g of LiAlH$_4$ and then the resulting mixture was refluxed for 1 hour. While ice-cooling the mixture, 130 ml of 0.8 N-NaOH were added to decompose the catalyzer and then filtered to remove a formed precipitate. The filtrate was washed with ethyl acetate/CH$_2$Cl$_2$ and concentrated under a reduced pressure. The remaining oily substance was separated and refined through a silica gel column chromatography (CH$_2$Cl$_2$-ethyl acetate) to obtain 84.0 g (67.6%) of a light yellowish oily substance. The substance was converted into hydrochloride in methanol in a conventional manner and recrystallized from methanol/methylethylketone to obtain the objective compound (hydrochloride) as colorless prism crystals having melting point of 198°–204° C. This salt can be converted into free base in a conventional manner.

Elementary Analysis: C$_{27}$H$_{32}$N$_2$O$_2$.2HCl; Cal. C 66.25, H 7.00, N 5.72; Found C 66.30, H 7.15, N 5.82.

IR ($\nu_{max}^{KBr}$) cm$^{-1}$:

2820 (OCH$_3$), 2560 (>N$^{\oplus}$<), 1250 (—O—)

MS:

EI/DI (m/z); 416 (M$^+$), 240 (base)

CI/DI (i-Bu) (m/z); 417 (M+1)

High MS (m/z); C$_{27}$H$_{32}$N$_2$O$_2$ (M$^+$)

Cal. 416, 2461

Found 416, 2433

NMR (CDCl$_3$) δ ppm:

7.45–6.75 (12H, m, Ar—H)

5.21 (1H, s, C1-H)

4.07 (2H, s, C6-H)

3.75 (3H, s, OCH$_3$)

3.1–2.7 (8H, m, methylene-H)

2.25 (3H, s, N—CH$_3$)

EXAMPLE 3

5-[3-(p-fluorobenzoyl)propyl]-1,2,3,4,5,6-hexahydro-1-phenyl-2-methyl-2,5-benzodiazocine (Compound I-c) (hydrochloride)

50 g (0.21 mol) of 1,2,3,4,5,6-hexahydro-1-phenyl-2,5-benzodiazocine, 56 g (0.23 mol) of 4,4-ethylenedioxy-4-(p-fluorophenyl)-butyl chloride, 26.5 g (0.315 mol) of NaHCO$_3$ and 373 ml of dimethylformamide were stirred at 100° C. for 4 hours and then subjected to distillation under a reduced pressure to remove the solvent. To the remaining substance, ethyl ether/water was added to extract the reaction products which was washed with water and dried on Na$_2$SO$_4$. The solvent therein was distilled off and then the remaining oily substance was separated and refined through a silica gel column chromatography (ethyl ether-ethyl ether/triethylamine=10/15) to obtain 76 g of an oily substance.

To a mixture of 4.00 g (8.97 mmol) of the oil, 1.18 g (11.7 mmol) of triethylamine and 100 ml of CHCl$_3$, 30 ml CHCl$_3$ solution of 1.07 g (9.87 mmol) of ClCOOC$_2$H$_5$ were added in dropwise for 1 hour, while stirring under inert gas atmosphere. The reaction mixture was washed with water, dried on Na$_2$SO$_4$ and subjected to distillation under a reduced pressure to remove the solvent. The remaining oily substance was dissolved in a mixture of 300 ml of ethyl ether and 100 ml of tetrahydrofuran and in the solution, 4 g of LiAlH$_4$ were added at 0° C. under inert gas atmosphere. The mixture was refluxed for 4 hours, while stirring same under inert gas atmosphere and then ice-cooled to add 0.8 N-NaOH for causing decomposition of the catalyzer. The reaction mixture was filtered to remove a formed precipitate. The filtrate was washed with ethyl acetate/CHCl$_3$ and condensed under a reduced pressure. The remaining oily substance was dissolved in methanol, 100 ml of 3 N-HCl were added thereto and then the mixture was stirred at room temperature for 15 minutes. Thereafter the solution was made into an alkali state by adding ammonia, extracted with CHCl$_3$, washed with water, dried on Na$_2$SO$_4$, subjected to distillation under a reduced pressure to remove the solvent and then refined through a silica gel column chromatography (triethylamine/ethyl ether/n-hexane=1/1/10) to obtain 2.42 g (52.6%) of substantially colorless oily substance.

The oil was treated by hydrogen chloride in methanol to convert the same into hydrochloride and recrystallized from 5% water/methanol/methylethylketone to obtain the objective compound (hydrochloride) as colorless prism crystals having melting point of 186°–192° C. (dec.). The salt may be converted into free base in a conventional manner.

Elementary Analysis: C$_{27}$H$_{29}$FN$_2$O.2HCl; Cal. C 66.26, H 6.38, N 5.72; Found C 65.88, H 6.59, N 5.42.

IR ($\nu_{max}^{KBr}$) cm$^{-1}$:

2450 (NH$^+$), 1680 (C=O)

MS:

EI/DI (m/z); 416 (M$^+$), 210 (base)

CI/DI (i-Bu) (m/z); 417 (M+1)

High MS (m/z); C$_{27}$H$_{29}$FN$_2$O (M$^+$)

Cal. 416, 2264

Found 416, 2272

NMR (CDCl$_3$) δ ppm:

8.2–7.8 (2H, m, C2', 6'-H)

7.6–6.6 (11H, m, Ar—H)

5.26 (1H, s, C1-H)

4.02 (2H, s, C6-H)

3.3–1.8 (10H, m, —CH$_2$ and NCH$_2$CH$_2$CH$_2$—)

2.28 (3H, s, N—CH$_3$)

EXAMPLE 4

5-cyclopropylmethyl-1,2,3,4,5,6-hexahydro-1-phenyl-2,5-benzodiazocine (Compound I-d) (hydrochloride)

To a mixture of 72.5 g (304.2 mmol) of 1,2,3,4,5,6-hexahydro-1-phenyl-2,5-benzodiazocine, 56 ml (d≃0.72, 398.4 mmol) of triethylamine and 1 liter of CHCl$_3$, 220 ml CHCl$_3$ solution of 35 g (334.8 mmol) of cyclopropanecarbonylchloride were added in dropwise for 1.5 hours at internal temperature of −30° C., while stirring under inert gas atmosphere. Thereafter, the mixture was further stirred at 0° C. for 1 hour and then washed with water, dried on Na$_2$SO$_4$ and distilled off the solvent therefrom.

The remaining oily substance was dissolved in 400 ml of anhydrous tetrahydrofuran and the resulting solution was added in dropwise for 1.5 hours at room temperature and under inert gas atmosphere into 1.2 liter ethyl ether suspension of 30 g of LiAlH$_4$ to reflux the mixture for 1 hour. The reaction mixture was ice-cooled and 130 ml of 1 N-NaOH were added thereto to decompose the catalyzer. After having filtered off a formed precipitate, the filtrate was washed with ethyl acetate/CH$_2$Cl$_2$ and concentrated under a reduced pressure. The remaining oily substance was refined through a silica gel column chromatography (ethyl ether-ethyl ether/triethylamine=10/1) to obtain 83 g (93.3%) of a light yellowish oily substance. The oil was treated by hydrogen chloride in methanol and crystallized from 3% water/methanol/methylethylketone to obtain the objective compound (hydrochloride) as colorless prism crystals having melting point of 234° to 240° C. (dec.). This salt may be converted into free base in a conventional manner.

Elementary Analysis: C$_{20}$H$_{24}$N$_2$.2HCl$\frac{1}{4}$H$_2$O; Cal. C 64.95, H 7.22, N 7.57; Found C 64.87, H 7.18, N 7.51.
IR ($\nu_{max}^{KBr}$) cm$^{-1}$:
2700, 2600 (NH$^+$)
MS:
  MI/DI (m/z); 292 (M$^+$), 221 (base)
  CI/DI (i-Bu) (m/z); 293 (M+1)
  High MS (m/z); C$_{20}$H$_{24}$N$_2$ (M$^+$)
    Cal. 292, 1936
    Found 292, 1929
NMR (CDCl$_3$) δ ppm:
  7.6–6.6 (9H, m, Ar—H)
  5.55 (1H, s, C1-H)
  4.26 (2H, ABq, J=13.0 Hz, Δν=20 Hz, C6-H$_2$)
  3.2–2.0 (6H, m, —CH$_2$— and

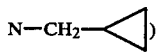

1.77 (1H, s, NH, disappear by adding D$_2$O)
  1.3–0.0 (5H, m,

EXAMPLE 5

[5(E)]-ethyl-4-[[4-[2-(1,2,3,4,5,6-hexahydro-1-phenyl-2,5-benzodiazocine)-5-yl]ethyl]phenyl]amino-4-oxo-2-butenoate (Compound I-e) (hydrochloride)

A mixture of 8.00 g (33.6 mmol) of 1,2,3,4,5,6-hexahydro-1-phenyl-2,5-benzodiazocine, 8.51 g (37.0 mmol) of p-nitrophenethylbromide, 4.23 g (50.4 mmol) of NaHCO$_3$ and 60 ml of dimethylformamide was stirred at 100° C. for 10 hours under inert gas atmosphere and then subjected to distillation to remove the solvent therein. After having added 150 ml of water, the reaction mixture was extracted with CHCl$_3$, washed with water, dried on Na$_2$SO$_4$, subjected to distillation to remove the solvent and refined through a silica gel column chromatography (ethyl ether/n-hexane=1/1-triethylamine/ethyl ether=1/10) to obtain 10.5 g (80.7%) of nitrophenethyl compound. 5.54 g (14.3 mmol) of this compound were dissolved in 25 ml of CHCl$_3$ and 150 ml of methanol were added therein. After having added 1 g of 10% Pd-C under inert gas atmosphere, the mixture was stirred at room temperature for 3 hours under hydrogen gas atmosphere and then filtered off the catalyst. The filtrate was concentrated under a reduced pressure, treated by hydrogen chloride in methanol to form hydrochloride and then recrystallized same from methanol/methylethylketone to obtain 6.60 g (99.0%) of aminophenethyl compound as colorless prism crystals having melting point of 252°–258° C. (dec.).

2.93 g (8.21 mmol) of free base of compound were dissolved in 100 ml of tetrahydrofuran and then 30 ml tetrahydrofuran solution of 1.47 g (9.03 mmol) of ethyl-3-(chloroformyl)acrylate was added therein in dropwise for 30 minutes at 0° C. After having stirred 1 hour, the reaction mixture was concentrated under a reduced pressure and 100 ml of water were added thereto. The solution was made into alkali state with ammonia, extracted with CHCl$_3$, washed with water, dried over Na$_2$SO$_4$, subjected to distillation to remove the solvent and refined through a silica gel column chromatography (triethylamine/ethyl acetate/n-hexane=0.5/1/5-0.3/2/1) to obtain 2.97 g (74.8%) of the objective compound (free base). The free base was treated by hydrogen chloride in methanol and recrystallized from water/methanol/methylethylketone to obtain the desired compound (hydrochloride) as colorless prism crystals having melting point of 248°–255° C. (dec.). This salt may also be converted into the free base in a conventional manner.

Elementary Analysis: C$_{30}$H$_{33}$N$_3$O$_3$.2HCl; Cal. C 64.75, H 6.34, N 7.55; Found C 64.52, H 6.49, N 7.26.
IR ($\nu_{max}^{KBr}$) cm$^{-1}$:
2480 (NH$^+$), 1700, 1675 (C=O)
MS:
  EI/DI (m/z); 483 (M$^+$), 194 (base)
  CI/DI (i-Bu) (m/z); 484 (M+1)
  High MS (m/z); C$_{30}$H$_{33}$N$_3$O$_3$ (M$^+$)
    Cal. 483, 2522
    Found 483, 2534
NMR (CDCl$_3$) δ ppm:
  8.40 (1H, br, N$\underline{H}$—CO, disappear by adding D$_2$O)
  7.7–6.6 (15H, m, Ar—H and olefinic proton)
  5.53 (1H, s, C1-H)
  4.28 (1H, ABq, J=13.0 Hz, Δν=20 Hz, C6-H$_2$)
  4.25 (2H, q, J=7.0 Hz, —C$\underline{H_2}$CH$_3$)
  3.2–2.5 (8H, m, —CH$_2$— and NCH$_2$CH$_2$Ar)
  1.93 (1H, br-s, NH, disappear by adding D$_2$O)
  1.30 (3H, t, J=7.0 Hz, —CH$_2$C$\underline{H_3}$)

EXAMPLE 6

5-[3-(p-fluorobenzoyl)propyl]-1,2,3,4,5,6-hexahydro-1-(p-methoxyphenyl)-2,5-benzodiazocine (Compound I-f)

10.72 g (39.95 mmol) of 1,2,3,4,5,6-hexahydro-1-(p-methoxyphenyl)-2,5-benzodiazocine, 10.27 g (41.97 mmol) of 4,4-ethylenedioxy-4-(p-fluorophenyl)-butyl chloride, 4.2 g (50.00 mmol) of NaHCO$_3$ and 250 ml of dimethylformamide were stirred at 145° C. for 4 hours and then the solvent was distilled off. After having added 30 ml of CH$_2$Cl$_2$ and 300 ml of ethyl ether, filtered off insoluble materials and distilled off the filtrate, the remaining oily substance was refined through a silica gel column chromatography (ethyl ether-ethyl ether/triethylamine=10/1) to obtain 15.8 g (83.0%) of the objective compound (free base) as substantially colorless oil. To the oil, 450 ml of methanol, 180 ml of water and 60 ml of conc. HCl were added, refluxed for 1 hour with stirring, distilled off the solvent and then the residue was recrystallized from water/ethanol to obtain 16.5 g (81.7%) of the desired compound (hydrochloride) as colorless prism crystals having melting point of 217°–234° C. (dec.). The salt may also be converted into the free base in a conventional manner.

Elementary Analysis: $C_{27}H_{29}FN_2O_2 \cdot 2HCl$; Cal. C 64.16, H 6.18, N 5.54; Found C 64.31, H 6.31, N 5.55.
IR $(\nu_{max}^{KBr})$ cm$^{-1}$:
2700-2600 (>N$^{\oplus}$<), 1685 (C=O)
MS:
EI/DI (m/z); 432 (M+), 251 (base)
CI/DI (i-Bu) (m/z); 433 (M+1)
High MS (m/z); $C_{27}H_{29}FN_2O_3$ (M+)
Cal. 432, 2211
Found 432, 2185
NMR (CDCl$_3$) δ ppm:
8.3-7.72 (2H, m, 2,6 positions in benzoyl)
7.5-6.68 (10H, m, Ar—H)
5.42 (1H, br-s, C1-H)
4.16 (2H, ABq, J=12.6 Hz, Δν=21.0 Hz, C6-H)
3.65 (3H, s, OCH$_3$)
3.18-2.35 (8H, m,

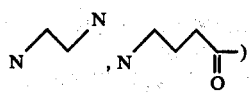

2.35-1.8 (2H, m,

1.65 (1H, br-s, NH, disappear by adding D$_2$O)

Physical Properties of Other Salts (1) 2.fumarate of Compound I-a
Crystalline form: colorless prism crystal;
Melting point: 164°-168° C. (dec.)
Elementary Analysis: $C_{28}H_{31}FN_2O_2 \cdot 2C_4H_4O_4$; Cal. C 63.70, H 5.79, N 4.13; Found C 63.71, H 5.85, N 4.16.

(2) 1,5-naphthalenedisulfonate of Compound I-a
Melting point: 205°-208° C. (dec.)
Elementary Analysis: $C_{28}H_{31}FN_2O_2 \cdot C_{10}H_8S_2O_6 \cdot H_2O$; Cal. C 60.62, H 5.49, N 3.72; Found C 60.23, H 5.37, N 3.80.

(3) 2.fumarate of Compound I-c
Crystalline form: colorless prism crystal
Melting point: 149°-153° C. (dec.)
Elementary Analysis: $C_{27}H_{29}FN_2O \cdot 2C_4H_4O_4$; Cal. C 64.81, H 5.75, N 4.32; Found C 64.66, H 5.80, N 4.37.

(4) 1,5-naphthalenedisulfonate of Compound I-c
Melting point: 230°-234° C. (dec.)
Elementary Analysis: $C_{27}H_{29}FN_2O \cdot C_{10}H_8S_2O_6 \cdot H_2O$; Cal. C 59.99, H 5.58, N 3.78; Found C 60.26, H 5.40, N 3.94.

Pharmaceutical Tests (A) Analgetic Action
(i) Haffner's Method
In accordance with a usual manner, dd-male mice of 14 to 22 g were classified into groups, each having 10 mice, compounds to be tested in various concentrations were given to each mouse and then clamped a tail root of the mouse with use of Koffer clamps in each time period of having lapsed 15, 30, 45 and 60 minutes from the dosage to measure an analgetic action of the compounds by judging as "negative" when the tested mouse cries or looks back.

Further the number of deaths was counted in each 10 mice group after having lapsed 2 hours from dosage of each testing agent into abdominal cavity and then ED$_{50}$, LD$_{50}$ and 95% confidence limit were calculated based on the Richfield and Wilcoxson Methods to compare the results obtained on the agents.

(ii) Acetic Acid Stretching Method
The dd-male mice of 17 to 23 g were classified into groups, each having 10 mice, and 0.7% aqueous solution of acetic acid was dosed into abdominal cavity for each mouse in a ratio of 10 ml/kg and then a stretching condition was observed over 5 minutes of having lapsed 10 to 15 minutes from the dosage. The test was repeated 4 times to obtain total measured value and an inhibition ratio was measured from number of stretching actions. A judgement has been given in "Yes" or "No" system.

According to the Richfield and Wilcoxson Methods, ED$_{50}$, LD$_{50}$ and 95% confidence limit were calculated and compared the same for each testing agents and Control.

Each testing agent and control was orally given 30 minutes before the dosage of the acetic acid in a ratio of 100 mg/10 ml/kg.

(B) Cough Curing Action
To each Hartley type guinea pig of 300 to 450 g, 0.5 ml/kg of menbutal was dosed into abdominal cavity to lightly anesthetize. Thereafter, the trachea was exposed by a throat surgical operation and a pin-hole was formed therein so as to allow an insertion of a hog bristle therein. The guinea pigs who have a cough in each time when the bristle was inserted into the pin-hole after having lapsed 5 and 20 minutes from the surgical operation were employed for the test. Measurements of the cough curing action were carried out in each time of having lapsed 30, 45, 60, 90 and 120 minutes from a dosage of agents to be tested into abdominal cavity in a ratio of 2.5 ml/kg (50 mg/kg). An inhibition ratio was determined based on total measured value in 6 times tests and a value measured before the dosage.

The inhibition ratio was classified into following 5 stages.

| | Inhibition Ratio | |
|---|---|---|
| (−) | | 0% |
| (±) | " | 0–10% |
| (+) | " | 10–20% |
| (++) | " | 20–35% |
| (+++) | " | more than 35% |

(C) Antipyretic Action
Wister type male rats of 100 to 140 g were classified into groups, each having 4 to 5 rats. The rats were abstrained from food for 1 day and then each rat was entered in each cage. The body temperature was measured under a constant room temperature through the rectum. This body temperature measurement was carried out in 3 times before a dosage of agents as well as after lapsed 30, 60, 90, 120 and 150 minutes from the dosage.

Judgements have been given based on following 5 measures.

(−) clearly showing no decrease in the body temperature,
(±) there is found a decrease in the body temperature but a notifiable difference can not be recognized,
(+) decrease in the body temperature is by 1.5° C. and obtained at least one result showing a notifiable difference of P<5%, or the decrease in the body temperature is by 1° C. only but show the value of P<1%, (++) showing decrease of 1° to 2° C. and obtaining at least one result of a notifiable difference of P<1%,
(+++) showing decrease of 2° to 3° C. and obtaining at least one result of a notifiable difference of P<0.1%.

(D) Effect on Sleep

The dd-type male mice of 16 to 24 g were classified into groups, each having 10 mice. To each mouse, a testing agent was dosed through abdominal cavity and after having lapsed 30 minutes from the dosage, 40 mg/kg of pentobarbital was also dosed through abdominal cavity to measure a time of sleeping period. The sleeping time in question designates a time period, wherein a facing reflex disappears. Judgements were given based on following 7 measures.

(– – –) sleeping time was shortened by 60 minutes or more in comparison with control,
(– –) sleeping time was shortened by 30 to 60 minutes in comparison with control,
(–) sleeping time was shortened by 10 to 30 minutes in comparison with control,
(±) sleeping time was shortened or extended by ±10 minutes in comparison with control,
(+) sleeping time was extended by 10 to 30 minutes in comparison with control,
(++) sleeping time was extended by 30 to 60 minutes in comparison with control,
(+++) sleeping time was extended by 60 minutes or more in comparison with control.

(E) Acute Toxity

The dd-type 5 weeks male mice of 21 to 26 g and Wister type 5 weeks male rats of 110 to 150 g were classified into groups, each having 10 mice or rats. After having given testing agents to the mice and rats, general conditions, number of deaths in each day and body weight changes have been observed over 7 days. An $LD_{50}$ value was calculated based on total number of deaths during the 7 days testing time period, in accordance with the Richfield-Wilcoxson Method. The surviving animals were dissected to visually observe internal organs thereof.

The following table shows results obtained through the tests as given above.

The agents according to the invention employed for the tests were hydrochlorides of the identified compounds.

| Compounds or agents (Example No.) | Analgetic Action | | | | Cough Curing Action in abdominal cavity 50 mg/Kg | Antipyretic Action in abdominal cavity 50 mg/Kg |
|---|---|---|---|---|---|---|
| | Acetic Acid Stretching Method | | Haffner's Method | | | |
| | $ED_{50}$ | | $ED_{50}$ | | 25 mg/Kg | |
| I-a (1) | 24.3 ~ 67.5 | 40.5 | 13.2 ~ 25.8 | 18.4 | ++ | ++ |
| I-b (2) | 31.7 ~ 74.2 | 48.5 | 20.2 ~ 34.1 | 26.2 | + | ++ |
| I-c (3) | 1.6 ~ 20.1 | 5.7 | 29.6 ~ 66.0 | 44.2 | + | ++ |
| I-d (4) | 8.6 ~ 21.3 | 13.5 | 11.7 ~ 25.0 | 17.1 | — | ++ |
| I-e (5) | 32.6 ~ 114.4 | 61.1 | 52.7 ~ 122.4 | 80.3 | — | ++ |
| I-f (6) | 6.2 ~ 21.4 | 11.5 | 22.7 ~ 41.6 | 30.7 | — | ++ |
| Nefopam (Control) | | | | | ++ (25 mg/Kg) | ++ |

| Compounds or agents (Example No.) | Sleep Incrementing Action | | Acute Toxity (mg/Kg) | | | | |
|---|---|---|---|---|---|---|---|
| | Oral dosage 100 mg/Kg | in abdominal cavity 50 mg/Kg | Rat | | Mouse | | |
| | | | Oral dosage | Intravenous injectional dosage | Oral dosage | Intravenous injectional dosage | in abdominal cavity |
| I-a (1) | +++ | ++ | 3500 | 20.0 (19.3 ~ 20.7) | 1500 | 30.1 (28.7 ~ 31.5) | 178.8 (159.1 ~ 201.0) |
| I-b (2) | +++ | +++ | 4090 (3298 ~ 5072) | 20.7 (19.1 ~ 22.4) | 623 (560.3 ~ 692.8) | 33.0 (31.9 ~ 34.2) | 124.4 (114.4 ~ 135.2) |
| I-c (3) | +++ | +++ | >4000 | 23.8 (22.4 ~ 25.3) | 1700 (1250 ~ 2312) | 29.0 (26.8 ~ 31.4) | 207.8 (179.6 ~ 240.4) |
| I-d (4) | — | — | 485 (391 ~ 601) | 17.8 (16.8 ~ 18.8) | 215 (180.2 ~ 255.9) | 18.0 (16.7 ~ 19.5) | 51.6 (48.4 ~ 55.0) |
| I-e (5) | ++ | — | >5000 | — | 938 (751 ~ 1172) | — | >200 |
| I-f (6) | +++ | +++ | 2890 (2388 ~ 3497) | 19.8 (19.1 ~ 20.5) | 340 (291.1 ~ 397.1) | 35.9 (32.5 ~ 39.7) | 108.9 (102.8 ~ 115.4) |
| Nefopam | — | — | 595 | 18.0 | 356 | 36.8 | 72.4 |

| (Control) | (50 mg/Kg) | (25 mg/Kg) | (492 ~ 720) | (16.5 ~ 19.6) | (306 ~ 414) | (33.6 ~ 40.3) | (69.5 ~ 75.4) |

PHARMACEUTICAL AGENT PREPARING EXAMPLE 1

Tablets for oral dosage

| | |
|---|---|
| (1) Compound I-a (hydrochloride) | 40 (mg) |
| (2) Mannitol | 100 |
| (3) Starch | 100 |
| (4) Carboxymethylcellulose calcium | 10 |
| (5) Polyvinylpyrrolidone | 50 |
| (6) Magnesium stearate | 3 |

The components 1 to 3 and 5 were mixed and the component 4 dissolved in ethanol was added and mixed therewith. The resulting mixture was made granules by a granulating machine and after having dried the same, the component 6 was added and mixed therewith and then finally made into each 300 mg tablet by a punch having diameter of 10 mm.

The tablet can be dosed as it was but if necessary, a conventional easily soluble coating may be applied thereon.

PHARMACEUTICAL AGENT PREPARING EXAMPLE 2

Injectionally dosing agent

Compound I-a was dissolved in distilled water in a ratio of 15 mg/2.5 ml, filtered under a sterilized condition, filled in each ampule by 2 ml, each ampule fused closed and then sterilized at 130° C. for 40 minutes.

What is claimed is:

1. A 2,5-benzodiazocine derivative represented by a formula

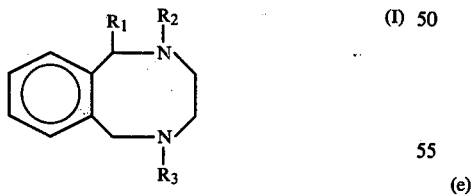

wherein $R_1$ is phenyl or p-methoxyphenyl, $R_2$ is hydrogen or methyl, and $R_3$ is methoxyphenethyl, 3-(p-fluorobenzoyl)-propyl, cyclopropylmethyl or

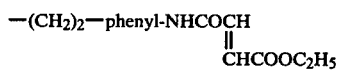

or a salt thereof.

2. A compound as claimed in claim 1, selected from the group consisting of (a)  (I-a)

(b)  (I-b)

(c)  (I-c)

(d)  (I-d)

(e)  (I-e)

and (f) 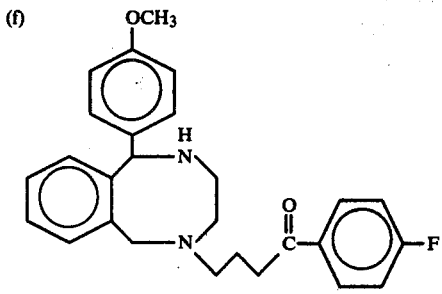 (I-f)

or a salt of the compound.

3. A pharmaceutical agent which comprises as an effective component at least one 2,5-benzodiazocine derivative represented by the formula

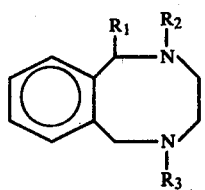 (I)

wherein $R_1$ is phenyl or p-methoxyphenyl, $R_2$ is hydrogen or methyl, and $R_3$ is methoxyphenethyl, 3-(p-fluorobenzoyl)-propyl, cyclopropylmethyl radical or

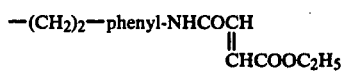

or salts of said derivatives.

4. The pharmaceutical agent as claimed in claim 3, wherein said effective component is at least one of the compounds represented by formulae (a) 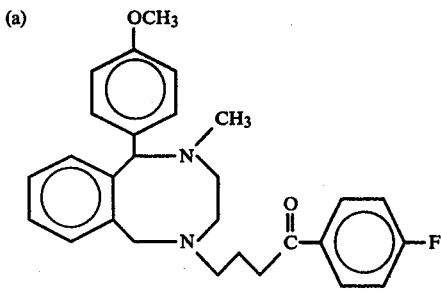 (I-a)

(b) 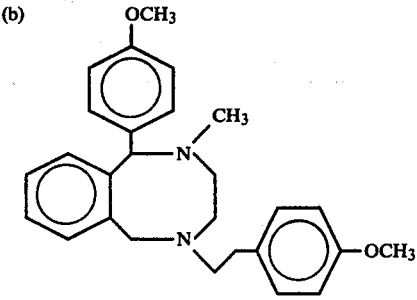 (I-b)

(c) 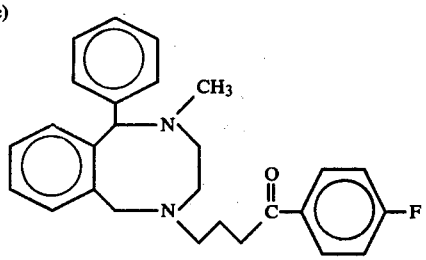 (I-c)

(d) 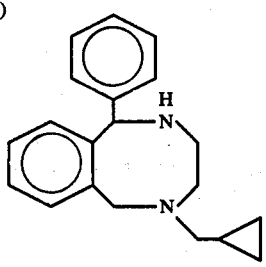 (I-d)

(e) 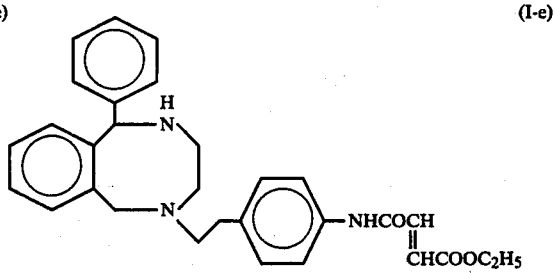 (I-e)

(f) 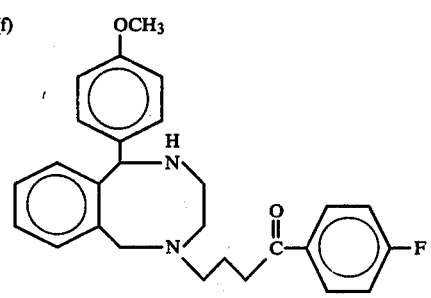 (I-f)

or a salt of said compound.

* * * * *